(12) United States Patent
Maeda

(10) Patent No.: US 9,389,239 B2
(45) Date of Patent: Jul. 12, 2016

(54) LIQUID-SAMPLE COLLECTING SYSTEM AND LIQUID-SAMPLE COLLECTING METHOD

(75) Inventor: Yoshiaki Maeda, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 109 days.

(21) Appl. No.: 13/463,367

(22) Filed: May 3, 2012

(65) Prior Publication Data

US 2012/0285268 A1 Nov. 15, 2012

(30) Foreign Application Priority Data

May 9, 2011 (JP) .................. 2011-104679

(51) Int. Cl.
*G01N 35/10* (2006.01)
*G01N 1/02* (2006.01)
*G01N 1/10* (2006.01)

(52) U.S. Cl.
CPC ............ *G01N 35/1009* (2013.01); *G01N 35/10* (2013.01); *G01N 1/02* (2013.01); *G01N 1/10* (2013.01)

(58) Field of Classification Search
CPC ......... G01N 1/10; G01N 35/00; G01N 35/10; G01N 35/1009; G01N 35/1011; G01N 35/1016; G01N 35/1065; G01N 35/1074; G01N 35/1004; G01N 35/00584; G01N 35/1067; G01N 35/1079; B01L 3/021
USPC ............. 73/863.01, 864, 863, 863.81, 61.59, 73/864.21, 61.55
See application file for complete search history.

(56) References Cited

U.S. PATENT DOCUMENTS 4,896,545 A * 1/1990 Averette .................... 73/863.01
4,938,383 A * 7/1990 Yamazaki ............ B01L 3/0293
222/41

(Continued)

FOREIGN PATENT DOCUMENTS

CN 1435687 A 8/2003
CN 101310188 A 11/2008

(Continued)

OTHER PUBLICATIONS

Chinese Office Action dated Sep. 26, 2013, issued in Chinese Patent Application No. 201210142781.9, w/partial English translation.

(Continued)

*Primary Examiner* — Hezron E Williams
*Assistant Examiner* — Marrit Eyassu
(74) *Attorney, Agent, or Firm* — Westerman, Hattori, Daniels & Adrian, LLP

(57) ABSTRACT

Provided is a liquid-sample collecting system and liquid-sample collecting method that can decrease the amount of carryover in the process of collecting a liquid sample while maintaining the efficiency of collecting the liquid sample. A liquid-sample collecting system according to the present invention includes: a sampling needle to be inserted into a sample container, for collecting a liquid sample contained in the sample container; a driver for moving the sampling needle; an input unit for allowing a user enter to information for setting the ascent speed of the sampling needle; an ascent-speed determiner for setting the ascent speed based on the entered information; and a controller for controlling the driver so as to move the sampling needle downward at a predetermined descent speed in a descent phase and upward at the aforementioned ascent speed in an ascent phase.

2 Claims, 4 Drawing Sheets

(56) References Cited

U.S. PATENT DOCUMENTS

| | | | |
|---|---|---|---|
| 5,395,588 A * | 3/1995 | North, Jr. | G01N 15/1404 422/67 |
| 6,363,802 B1 * | 4/2002 | Grippo et al. | 73/864.24 |
| 2002/0142483 A1 * | 10/2002 | Yao et al. | 436/180 |
| 2007/0144253 A1 * | 6/2007 | Kobayashi | 73/304 C |
| 2007/0157709 A1 * | 7/2007 | Gamble et al. | 73/61.55 |
| 2009/0000401 A1 * | 1/2009 | Oonuma | 73/864.11 |
| 2009/0044607 A1 * | 2/2009 | Hochgraeber et al. | 73/61.55 |
| 2009/0100942 A1 * | 4/2009 | Maeda et al. | 73/863.01 |
| 2010/0000338 A1 * | 1/2010 | Van Berkel et al. | 73/863.01 |
| 2010/0056396 A1 * | 3/2010 | Van Dam et al. | 506/30 |
| 2010/0210007 A1 * | 8/2010 | Iwamura et al. | 435/286.2 |
| 2011/0209565 A1 * | 9/2011 | Tomita | 73/864.21 |
| 2013/0079247 A1 * | 3/2013 | Yao et al. | 506/12 |

FOREIGN PATENT DOCUMENTS

| | | | |
|---|---|---|---|
| JP | 64-047955 A | 2/1989 | |
| JP | 09-184846 | * 7/1997 | G01N 35/10 |
| JP | 09-184846 A | 7/1997 | |
| JP | 2886894 B2 | 4/1999 | |
| JP | 11-344498 A | 12/1999 | |
| JP | 2003-215118 A | 7/2003 | |

OTHER PUBLICATIONS

Office Action dated May 30, 2014, issued in Corresponding Chinese Patent Application No. 201210142781.9, with English Translation (10 pages).

Chinese Office Action dated Oct. 11, 2014, issued in corresponding Chinese Patent Application No. 201210142781.9, w/ English translation (11 pages).

Notice of Rejection dated Apr. 27, 2015, issued in counterpart Chinese Patent Application No. 201210142781.9, with partial English translation (8 pages).

* cited by examiner

Fig. 3

| USED UNIT | PRODUCT NAME |
|---|---|
| DEGASSER | DGU-20A5 |
| PUMP | LC-30AD |
| FLOW RATE | 0.6 mL/min |
| MIXER | MR 20 µL |
| AUTOSAMPLER | SIL-30ACMP |
| INJECTED AMOUNT | 5 µL |
| NEEDLE CLEANING | NOT PERFORMED |
| OVEN | CTO-30AS |
| COLUMN TEMPERATURE | 40 °C |
| COLUMN | XR-ODSIII 2×50 mm 1.6 µm |
| UV DETECTOR | SPD-20A |
| DETECTION WAVELENGT | 272 nm |
| AUX RANGE | 1.0 AU/V |
| RESPONSE | 0.1 sec |
| SYSTEM CONTROLLER | CBM-20A lite |
| DATA PROCESSING | LabSolutions V5.32SP1 |
| SAMPLING TIME | 10 ms |
| CHANNEL | Ch1(272 nm) |
| WIDTH | 5 sec |
| SLOPE | 200 µV/min |
| DRIFT | 0 µV/min |
| T.DBL | 1,000 min |
| MINIMUM AREA/HEIGHT | 20 counts |
| USED DATA | Area |

Fig. 4
| | RETENTION TIME (min) | AREA | HEIGHT | CARRYOVER |
|---|---|---|---|---|
| BLANK SOLUTION | NOT DETECTED | NOT DETECTED | NOT DETECTED | |
| CAFFEINE 20mg/L | 0.507 | 253,251 | 173,569 | |
| CAFFEINE 4,000mg/L | | (50,650,200) | HIGHER THAN DETECTION LIMIT | |
| BLANK SOLUTION (1ST) | 0.498 | 227 | 97 | 0.0004% |
| BLANK SOLUTION (2ND) | 0.499 | 120 | 56 | 0.0002% |
| BLANK SOLUTION (3RD) | 0.497 | 89 | 48 | 0.0002% |
| BLANK SOLUTION (4TH) | 0.496 | 92 | 37 | 0.0002% |
| BLANK SOLUTION (5TH) | 0.508 | 53 | 29 | 0.0001% |
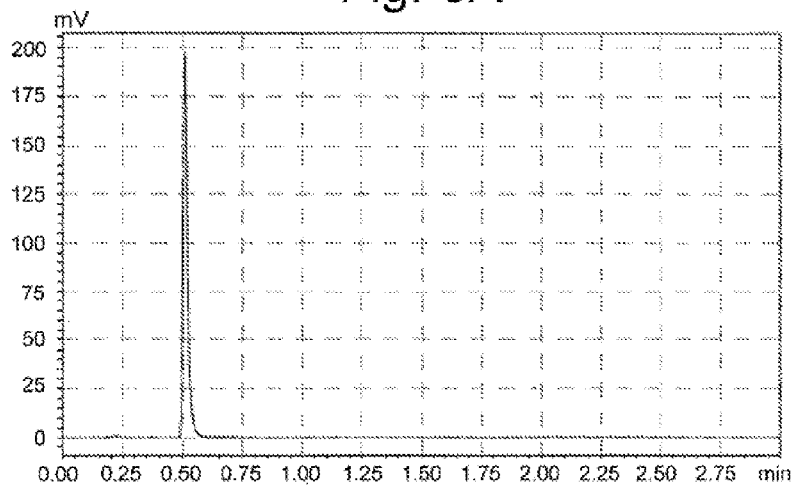
Fig. 5A
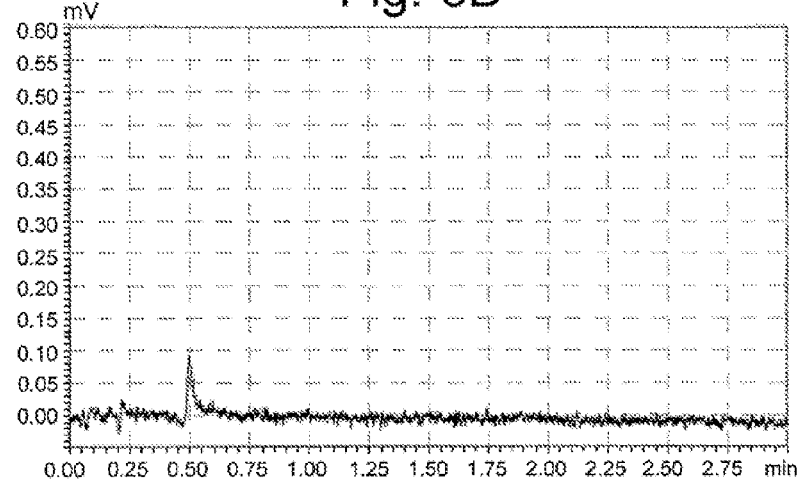
Fig. 5B FIG. 6 (Prior Art)
| | RETENTION TIME (min) | AREA | HEIGHT | CARRYOVER |
|---|---|---|---|---|
| BLANK SOLUTION | NOT DETECTED | NOT DETECTED | NOT DETECTED | |
| CAFFEINE 20mg/L | 0.505 | 252,391 | 187,717 | |
| CAFFEINE 4,000mg/L | | (50,478,200) | HIGHER THAN DETECTION LIMIT | |
| BLANK SOLUTION (1ST) | 0.492 | 673 | 404 | 0.0013% |
| BLANK SOLUTION (2ND) | 0.494 | 603 | 392 | 0.0012% |
| BLANK SOLUTION (3RD) | 0.494 | 671 | 449 | 0.0013% |
| BLANK SOLUTION (4TH) | 0.493 | 888 | 542 | 0.0018% |
| BLANK SOLUTION (5TH) | 0.494 | 645 | 427 | 0.0013% |
FIG. 7A (Prior Art)
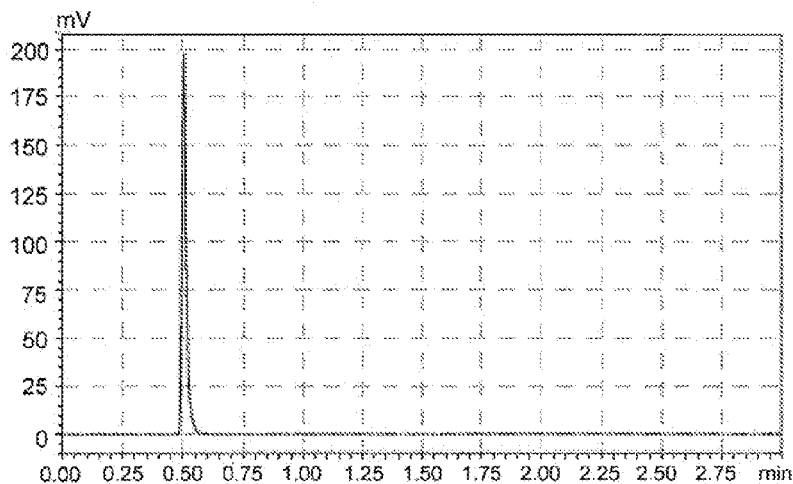
FIG. 7B (Prior Art)
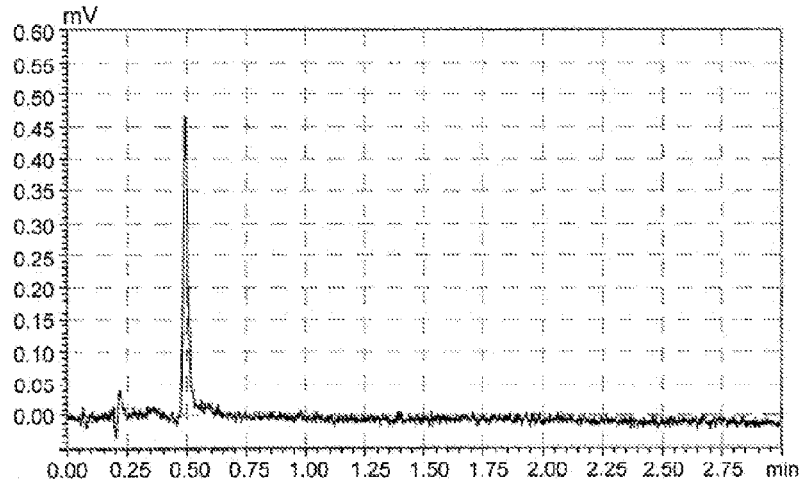

LIQUID-SAMPLE COLLECTING SYSTEM AND LIQUID-SAMPLE COLLECTING METHOD

TECHNICAL FIELD

The present invention relates to a method and system for collecting a liquid sample. More specifically, it relates to a liquid-sample collecting system and a liquid-sample collecting method suitable for collecting a sample for a liquid chromatograph.

BACKGROUND ART

A process for collecting a liquid sample from a sample vial in a liquid chromatograph analyzer system is as follows: A sampling needle is moved downward, penetrating through the septum of the sample vial, until its tip is immersed in the liquid sample. At this position, the liquid sample is sucked into the needle. Then, the sampling needle holding the liquid sample is moved upward to pull up its tip from the surface of the liquid sample and further upward until it is pulled out of the septum. Subsequently, the sampling needle is transferred to a predetermined sample injection point, where the liquid sample is injected into the mobile phase.

Liquid chromatograph analyzer systems are used to serially analyze many liquid samples. One conventional technique for reducing the time required for the analysis is to increase the speed of the vertical movements of the sampling needle to improve the efficiency of collecting the liquid sample. This technique has been made possible with the improvement in the performance of the motor.

BACKGROUND ART DOCUMENT

Patent Document

Patent Document 1: JP-A 2003-215118

SUMMARY OF THE INVENTION

Problem to be Solved by the Invention

However, if the sampling needle is moved upward at a high speed, the liquid sample attaching onto the outer wall of the sampling needle having its tip immersed in the liquid sample in the vial cannot be sufficiently detached from that wall at the stage where the sampling needle has been completely pulled up from the liquid surface. By further pulling the sampling needle, the largest portion of the remaining liquid sample can be scraped off the outer wall of the sampling needle by the septum. However, a portion of the liquid sample remains there, forming a thin film. The amount of liquid sample remaining on the outer wall in this manner increases with the ascent speed of the sampling needle.

A conventional technique for decreasing the amount of liquid sample remaining on the outer wall of the sampling needle is to use a sampling needle made of a resin or a noble metal with a low level of wettability to liquid samples. However, these types of sampling needles are expensive and yet cannot sufficiently lower the attaching force for all of the various kinds of liquid samples.

Using a sampling needle with a liquid sample remaining on its outer wall causes carryover; i.e. the previous liquid sample is mixed in the next sample in the subsequent sample-collecting operation and wrongly detected in the measurement.

The liquid sample on the outer wall of the sampling needle can be washed off by soaking the sampling needle in a cleaning liquid. However, such a system is inefficient since it requires additionally providing a washing tank and a cleaning process.

The problem to be solved by the present invention is to decrease the amount of carryover while maintaining the efficiency of collecting the liquid sample.

Means for Solving the Problems

A liquid-sample collecting system according to the present invention aimed at solving the aforementioned problem includes:

a sampling needle to be inserted into a sample container for collecting a liquid sample contained in the sample container;

a driver for vertically moving the sampling needle;

an input unit for allowing a user to enter information for setting an ascent speed of the sampling needle;

an ascent-speed determiner for determining the ascent speed based on the entered information; and a controller for controlling the driver so as to move the sampling needle downward at a predetermined descent speed in a descent phase, and upward at the aforementioned ascent speed in an ascent phase.

For example, the information for setting the ascent speed of the sampling needle may be a value directly indicating the ascent speed of the sampling needle, or it may be information corresponding to the kind of liquid sample, as will be described later.

By the liquid-sample collecting system according to the present invention, the ascent speed of the sampling needle can be appropriately changed, while the descent speed of the same needle can be as high as in the conventional case.

While the sampling needle is being pulled up from the liquid surface in the sample container, the liquid sample attaches onto the outer wall of the sampling needle due to its surface tension, ultimately being dragged upward with the ascent of the needle. Meanwhile, the portion of the liquid sample being dragged upward from the liquid surface is pulled downward by a gravitational force. The amount of liquid sample to be dragged up from the liquid surface depends on the balance between the two forces. From the dynamic point of view, the amount of liquid sample to be dragged up from the liquid surface increases when the sampling needle is pulled at a higher speed, and decreases when the pulling speed is lowered. Accordingly, it is possible to adequately detach the liquid sample from the outer wall of the sampling needle by appropriately decreasing the ascent speed of the sampling needle.

The previously described theory directly applies to the case where the sampling needle is inserted into the liquid sample and pulled up from the liquid surface without penetrating through the septum. The same theory also applies to the case of inserting the sampling needle through the septum into the liquid sample. In this case, pulling the sampling needle at a higher speed causes a larger amount of liquid sample that is scraped off by the septum and remain on its inside, which results in a corresponding increase in the amount of liquid attaching onto the outer surface of the sampling needle without being scraped off by the septum. This situation occurs as follows: As the speed of the needle relative to the septum increases, the liquid sample attaching onto the outer wall surface of the sampling needle becomes more difficult to be scraped off the outer wall due to dynamic viscosity. In this situation, the septum is likely to be stained with the liquid sample, allowing a considerable amount of liquid sample to remain on the needle and be carried to the outside.

On the other hand, the operation of moving the sampling needle downward can be performed at high speeds, as in the conventional case, since this operation does not influence the problem of the remnant sample attaching onto the outer wall of the sampling needle.

As a result, the amount of carryover can be decreased while maintaining the efficiency of collecting the liquid sample.

As already explained, the lower the ascent speed of the sampling needle, the easier the detachment of the liquid sample from the outer wall of the sampling needle. However, an excessive decrease in the ascent speed of the sampling needle significantly deteriorates the sample-collecting efficiency.

To address this problem, in a preferable mode of the system according to the present invention, the ascent-speed determiner has a previously created data table in which the kinds of liquid samples to be collected are related to the ascent speed, and automatically sets an optimal ascent speed by referring to the data table upon receiving, as the aforementioned information, a kind of liquid sample entered through the input unit by a user. For example, the data table can be created by determining the optimal ascent speed for each kind of liquid sample by a preliminary experiment. As another example, the data table may be created as a table for relating the kind of liquid sample to the ascent speed of the sampling needle taking into account the characteristic of the viscosity and/or density of the liquid sample.

With this system, users only need to select the kind of liquid sample; the sampling needle is automatically moved upward at the optimal speed for the selected kind of liquid sample. It is unnecessary for users to determine an optimal ascent speed for each different kind of liquid sample to be collected. Thus, the workload on the user is reduced.

A liquid-sample collecting method according to the present invention aimed at solving the aforementioned problem is a method for collecting a liquid sample in a sample container by vertically moving a sampling needle, including the steps of:

allowing a user to enter information for setting an ascent speed of the sampling needle;

determining the ascent speed based on the entered information; and moving the sampling needle downward at a predetermined descent speed in a descent phase, and upward at the aforementioned ascent speed in an ascent phase.

For example, the information for setting the ascent speed of the sampling needle may be a value directly indicating the ascent speed of the sampling needle, or it may be information corresponding to the kind of liquid sample, as will be described later.

By the liquid-sample collecting method according to the present invention, while the descent speed of the needle can be as high as in the conventional case, the ascent speed of the sampling needle can be appropriately changed so as to adequately detach the liquid sample from the outer wall of the sampling needle. Thus, the amount of carryover can be decreased while maintaining the efficiency of collecting the liquid sample.

Similar to the liquid-sample collecting system according to the present invention, the liquid-sample collecting method according to the present invention may preferably include the steps of preparing a data table in which the kinds of liquid samples to be collected are related to the ascent speed, and automatically setting an optimal ascent speed by referring to the data table upon receiving, as the aforementioned information, a kind of liquid sample entered by a user.

Effect of the Invention

By using the liquid-sample collecting system or liquid-sample collecting method according to the present invention, the amount of carryover can be decreased while maintaining the efficiency of the measurement. When the aforementioned data table is additionally used, users do not need to determine an optimal ascent speed for each different kind of liquid sample to be collected, so that the workload on the user will be reduced.

BRIEF DESCRIPTION OF THE DRAWINGS

FIG. 3 is a table showing the measurement conditions of an absorbance measurement using a liquid chromatograph system.

FIG. 4 is a table showing the results of absorbance measurements performed by a liquid-sample collecting method according to the present invention.

FIGS. 5A and 5B are graphs showing absorption spectrums obtained by a liquid-sample collecting method according to the present invention.

FIG. 6 is a table showing the results of absorbance measurements performed by a conventional liquid-sample collecting method.

FIGS. 7A and 7B are graphs showing absorption spectrums obtained by a conventional liquid-sample collecting method.

BEST MODE FOR CARRYING OUT THE INVENTION

Figure 1:
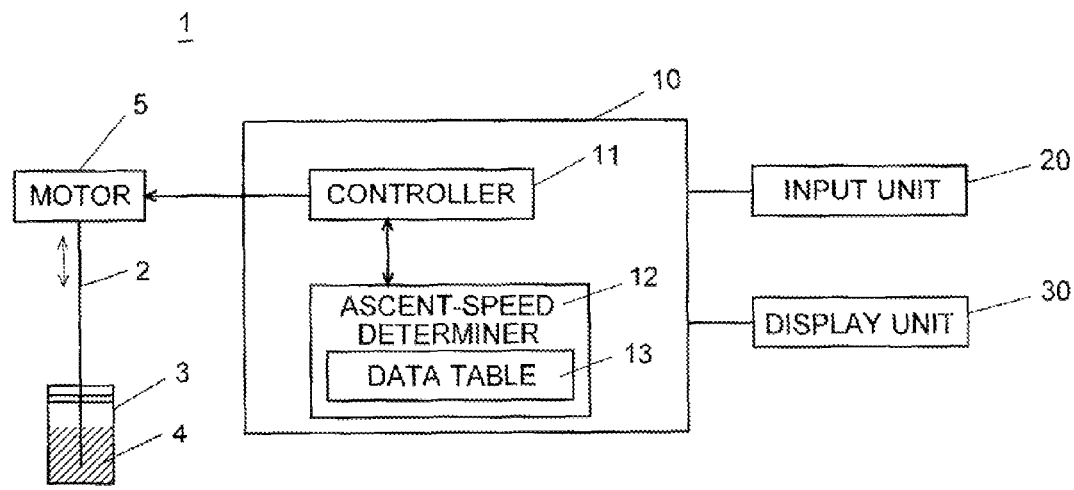
FIG. 1 is a diagram illustrating one embodiment of the liquid-sample collecting system according to the present invention.

One embodiment of the liquid-sample collecting system according to the present invention is hereinafter described by means of FIG. 1. The liquid-sample collecting system 1 of the present embodiment is a system for collecting a liquid sample 4 in a sample vial 3 by vertically moving a sample needle 2. This system has the sampling needle 2, a driver 5 including a motor for vertically moving the sampling needle 2, a controller 11 for controlling the operation of the driver 5, and an ascent-speed determiner 12 for setting the ascent speed of the sampling needle 2 by a process which will described later. The controller 11 and the ascent-speed determiner 12 are integrally configured by a computer 10 with a predetermined built-in program. An input unit 20 and a display unit 30 are connected to the computer 10.

In the controller 11, the descent speed of the sampling needle 2 is previously set so that the motor will operate at the highest speed when descending the needle 2. The ascent-speed determiner 12 has a built-in data table 13 in which the kind of liquid sample 4 is related to the ascent speed of the sampling needle 2.

Figure 2A:
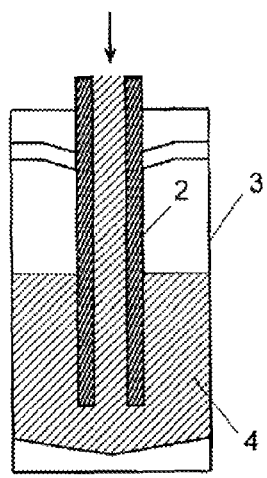
FIGS. 2A-2C are diagrams illustrating the process of collecting a liquid sample by vertically moving the sampling needle.
Figure 2B:
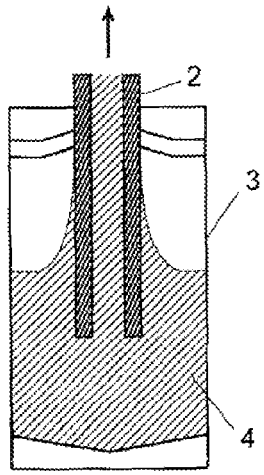
Figure 2C:
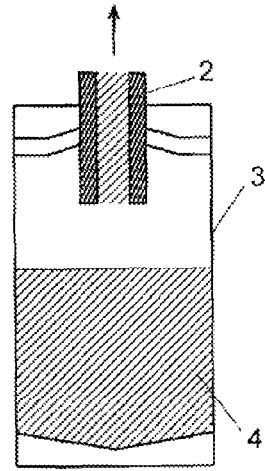

A process of collecting the liquid sample 4 by vertically moving the sampling needle 2 is illustrated in FIGS. 2A-2C. FIG. 2A shows the step of sucking the liquid sample 4 through the sampling needle 2 with its tip immersed in the liquid sample 4. FIGS. 2B and 2C show the process of moving the sampling needle 2 upward after the suction of the liquid sample 4.

When the sampling needle 2 is moved upward from the position where its tip is immersed in the liquid sample 4 (FIG. 2A), the liquid sample 4 attaches onto the outer wall of the sampling needle 2 due to surface tension, being dragged upward with the ascent of the sampling needle 2 while the sampling needle 2 is ascending from the liquid surface in the sample vial 3 (FIG. 2B). Meanwhile, the portion of the liquid sample 4 being dragged up from the liquid surface is pulled downward by a gravitational force. When the sampling needle 2 is further pulled upward, the liquid sample 4 in the sample vial 3 comes off the outer wall of the sampling needle 2 (FIG. 2C).

In the state shown in FIG. 2B, the amount of liquid sample 4 attaching onto the outer wall surface of the sampling needle 2 and being dragged up from the liquid surface is determined by the balance between the aforementioned two forces. From the dynamic point of view, the amount of liquid sample 4 to be dragged up from the liquid surface increases when the sampling needle is pulled at a higher speed, and decreases when the pulling speed is lowered. Accordingly, it is possible to adequately detach the liquid sample 4 from the outer wall of the sampling needle 2 by appropriately decreasing the ascent speed of the sampling needle 2.

The magnitudes of the aforementioned surface tension and gravitational force depend on the viscosity or density of the liquid sample 4. Accordingly, it is preferable to create the data table 13 as a table in which the kind of liquid sample is related to the ascent speed of the sampling needle taking into account the characteristic of the viscosity and/or density of the liquid sample.

An operation of the liquid-sample collecting system according to the present embodiment is hereinafter described.

Initially, the ascent-speed determiner 12 displays, on the display unit 30, a screen for allowing a user to specify the kind of liquid sample 4. On this screen, the user enters the kind of liquid sample 4 through the input unit 20. Upon this operation, the ascent-speed determiner 12 sets the ascent speed of the sampling needle 2 based on the built-in data table 13, and sends the ascent-speed information to the controller 11.

As already noted, the descent speed of the sampling needle 2 is previously set in the controller 11. After receiving the ascent-speed information from the ascent-speed determiner 12, the controller 11 controls the operation of the driver 5 so as to make the sampling needle 2 move downward at the previously set descent speed in the descent phase and upward at the aforementioned ascent speed in the ascent phase.

EXAMPLE

The effect of the liquid-sample collecting system and liquid-sample collecting Method according to the present invention has been confirmed as follows.

With the descent speed of the sampling needle set at 100 mm/sec and the ascent speed set at 40 mm/sec, 5 μL of solution containing caffeine at a concentration of 20 mg/L was collected from a sample vial. The collected solution was injected into the column of a liquid chromatograph system (SPD-20A, manufactured by Shimadzu Corporation) to perform an absorbance measurement of this solution. Subsequently, the absorbance measurement was similarly performed for 5 μL of solution containing caffeine at a concentration of 4,000 mg/L as well as for five 5 μL samples of blank solution. For each of the absorption spectrums obtained by the measurements, the area of the caffeine peak was calculated. Using the calculated values, the percentage of carryover, i.e. the percentage of caffeine mixed in the blank solution sampled after the collection of the 5 μL caffeine solution with a concentration of 4,000 mg/L, was calculated. The measurement conditions were as shown in FIG. 3, and the results of the absorbance measurements were as shown in FIG. 4. FIGS. 5A and 5B respectively show the absorption spectrum obtained by the measurement of the 5 μL caffeine solution with a concentration of 20 mg/L and the absorption spectrum obtained by the measurement of the first sample of the blank solution.

In the measurement of the 5 μL caffeine solution with a concentration of 4,000 mg/L, the peak exceeded the upper detection limit. Given this situation, the area of this peak was estimated to be equal to 200 times the peak area obtained in the absorption measurement of the 5 μL caffeine solution with a concentration of 20 mg/L. The estimated value was as shown in the parentheses in FIG. 4.

For comparison, the measurements were performed under the same conditions except for the speed of the sampling needle, which was moved at a high speed (100 mm/sec) in both directions as in the conventional cases. The results of these measurements were as shown in FIG. 6. FIGS. 7A and 7B respectively show the absorption spectrum obtained by the measurement of the 5 μL caffeine solution with a concentration of 20 mg/L and the absorption spectrum obtained by the measurement of the first sample of the 5 μL blank solution.

A comparison between the results of FIG. 4 and FIG. 6 demonstrates that the liquid-sample collecting method according to the present invention significantly decreases the percentage of the carryover as compared to the conventional liquid-sample collecting method. For example, the percentage of the carryover decreased from 0.0013% to 0.0004% in the case of the first sample of the blank solution, and from 0.0013% to 0.0001% in the case of the fifth sample of the blank solution. Comparing the spectrums shown in FIGS. 5B and 7B also demonstrates a significant decrease in the height of the peak originating from the carryover.

The previous embodiment is a mere example of the present invention and can be appropriately changed or modified within the spirit of the present invention. For example, although the liquid-sample collecting system of the previous embodiment had the display unit 30 on which a screen for entering the kind of liquid sample 4 is displayed by the ascent-speed determiner 12, it is possible to omit the display unit 30 and provide one or more buttons as the input unit 20 so that users can select the kind of liquid sample 4 by pressing the buttons. Furthermore, the data table 13 may be created by performing a preliminary experiment.

Although the system of the previous embodiment had the built-in data table 13 in the ascent-speed determiner 12, it is possible to omit the built-in data table 13 and let users manually enter the numerical value of the ascent speed. It is also possible to preset several levels of ascent speeds in the ascent-speed determiner 12 and let users select one of those speeds taking into account the kind of liquid sample 4.

In the case of collecting a low-viscosity or low-density liquid sample 4, it is possible that no significant carryover occurs even if the ascent speed of the sampling needle 2 is as high as the descent speed. Accordingly, it is possible to provide a switch for allowing users to appropriately select whether or not to use the liquid-sample collecting method according to the present invention, taking into account the kind of liquid sample 4.

EXPLANATION OF NUMERALS

1 . . . Liquid-Sample Collecting System
2 . . . Sampling Needle

3 . . . Sample Vial
4 . . . Liquid Sample
5 . . . Driver
10 . . . Computer
11 . . . Controller
12 . . . Ascent-Speed Determiner
13 . . . Data Table
20 . . . Input Unit
30 . . . Display Unit

The invention claimed is:

1. A liquid-sample collecting system, comprising:
a sampling needle to be inserted into a sample container through a septum for collecting a liquid sample contained in the sample container;
a driver for vertically moving the sampling needle;
an input unit for allowing a user to enter a kind of liquid sample to be collected for setting a first ascent speed of the sampling needle;
an ascent-speed determiner for determining the first ascent speed based on the kind of liquid sample entered by the user;
a switch for selecting the first ascent speed or a second ascent speed, the second ascent speed being equal to a predetermined descent speed; and
a controller for controlling the driver so as to move the sampling needle downward at the predetermined descent speed in a descent phase, and upward unidirectionally at the first ascent speed or the second ascent speed, which is selected through the switch, in an ascent phase,
wherein the ascent-speed determiner has a previously created data table in which kinds of liquid samples to be collected are related to optimal ascent speeds, and sets the optimal ascent speed as the first ascent speed by referring to the data table upon receiving the kind of liquid sample entered through the input unit by the user, the optimal ascent speed being determined so as to detach the liquid-sample from an outer wall of the sampling needle while a tip of the sampling needle is immersed in the liquid sample contained in the sample container, and the optimal ascent speed being slower than the predetermined descent speed, and
wherein the data table is a table for relating the kinds of liquid samples to the ascent speeds of the sampling needle taking into account a characteristic of a viscosity and/or density of the liquid samples.

2. A liquid-sample collecting method for collecting a liquid sample in a sample container by vertically moving a sampling needle, comprising steps of:
allowing a user to enter a kind of liquid sample to be collected for setting a first ascent speed of the sampling needle;
determining the first ascent speed based on the kind of liquid sample entered by the user;
selecting through a switch the first ascent speed or a second ascent speed, the second ascent speed being equal to a predetermined descent speed;
moving the sampling needle downward at the predetermined descent speed in a descent phase to insert the sampling needle into the sample container through a septum to collect the liquid sample, and upward unidirectionally at the first ascent speed or the second ascent speed, which is selected through the switch, in an ascent phase;
preparing a previously created data table in which kinds of liquid samples to be collected are related to the ascent speeds, and automatically setting an optimal ascent speed as the first ascent speed by referring to the data table upon receiving the kind of liquid sample entered by the user,
wherein the optimal ascent speed is determined so as to detach the liquid-sample from an outer wall of the sampling needle while a tip of the sampling needle is immersed in the liquid sample contained in the sample container, and the optimal ascent speed being slower than the predetermined descent speed, and
wherein the data table is a table for relating the kinds of liquid samples to the ascent speeds of the sampling needle taking into account a characteristic of a viscosity and/or density of the liquid samples.

* * * * *